US008892182B2

(12) United States Patent
Matonick

(10) Patent No.: US 8,892,182 B2
(45) Date of Patent: Nov. 18, 2014

(54) DOUBLE BALLOON ISOLATION CATHETERS AND METHODS THEREFOR

(75) Inventor: John P. Matonick, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 1570 days.

(21) Appl. No.: 12/028,147

(22) Filed: Feb. 8, 2008

(65) Prior Publication Data
US 2009/0203995 A1 Aug. 13, 2009

(51) Int. Cl.
A61B 5/05 (2006.01)
A61M 25/10 (2013.01)
A61M 25/00 (2006.01)
A61B 1/31 (2006.01)

(52) U.S. Cl.
CPC ... *A61M 25/1011* (2013.01); *A61M 2025/1052* (2013.01); *A61M 2210/1064* (2013.01); *A61M 25/007* (2013.01); *A61B 1/31* (2013.01)
USPC ... 600/407; 604/101.05; 604/919; 604/96.01; 604/509; 604/101.01; 600/115; 600/116

(58) Field of Classification Search
None
See application file for complete search history.

(56) References Cited

U.S. PATENT DOCUMENTS

| 3,937,224 | A | | 2/1976 | Uecker | |
|---|---|---|---|---|---|
| 4,180,076 | A | * | 12/1979 | Betancourt | 604/101.03 |
| 4,676,228 | A | * | 6/1987 | Krasner et al. | 600/116 |
| 4,690,131 | A | * | 9/1987 | Lyddy et al. | 600/115 |
| 4,932,956 | A | * | 6/1990 | Reddy et al. | 606/192 |
| 5,188,595 | A | * | 2/1993 | Jacobi | 604/509 |
| 5,217,439 | A | | 6/1993 | McClusky | |
| 5,234,454 | A | * | 8/1993 | Bangs | 606/191 |
| 5,411,479 | A | * | 5/1995 | Bodden | 604/101.03 |
| 5,613,949 | A | | 3/1997 | Miraki | |
| 5,653,240 | A | * | 8/1997 | Zimmon | 600/486 |
| 5,662,608 | A | | 9/1997 | Imran et al. | |
| 5,819,736 | A | * | 10/1998 | Avny et al. | 600/407 |
| 5,820,595 | A | * | 10/1998 | Parodi | 604/101.05 |
| 5,919,163 | A | * | 7/1999 | Glickman | 604/101.05 |
| 6,077,257 | A | * | 6/2000 | Edwards et al. | 604/506 |
| 6,221,006 | B1 | * | 4/2001 | Dubrul et al. | 600/159 |
| 6,471,672 | B1 | | 10/2002 | Brown et al. | |
| 6,575,932 | B1 | | 6/2003 | O'Brien et al. | |
| 6,706,013 | B1 | | 3/2004 | Bhat et al. | |
| 2002/0065507 | A1 | * | 5/2002 | Zadno-Azizi | 604/509 |
| 2003/0195537 | A1 | * | 10/2003 | Dubrul et al. | 606/159 |
| 2004/0186349 | A1 | * | 9/2004 | Ewers et al. | 600/114 |
| 2005/0038419 | A9 | * | 2/2005 | Arnold et al. | 606/15 |
| 2005/0101837 | A1 | * | 5/2005 | Kalloo et al. | 600/115 |

(Continued)

FOREIGN PATENT DOCUMENTS

WO  WO 0205887 A2 *  1/2002
WO  WO 2007086073 A2 *  8/2007

*Primary Examiner* — Nicholas Evoy

(57) ABSTRACT

A system for examining a colon includes a catheter, such as a rectal catheter, having a proximal end, a distal end, and a central lumen extending from the proximal end to the distal end of the catheter, and a flexible tube coupled with the catheter. The system includes a first balloon located adjacent a distal end of the flexible tube, and a second balloon extending around the catheter and being located between the distal and proximal ends of the catheter, whereby the distance between the first and second balloons is adjustable by sliding the flexible tube through the central lumen of the catheter. The first and second balloons are inflatable for isolating a section of a colon, and a gas or contrast agent may be introduced into the isolated colon section for conducting the examination.

20 Claims, 13 Drawing Sheets

(56) References Cited

U.S. PATENT DOCUMENTS

| | | | |
|---|---|---|---|
| 2005/0107664 A1* | 5/2005 | Kalloo et al. | 600/115 |
| 2005/0131500 A1* | 6/2005 | Zalesky et al. | 607/89 |
| 2005/0154355 A1* | 7/2005 | Gross et al. | 604/232 |
| 2005/0158899 A1* | 7/2005 | Jacobsen et al. | 438/29 |
| 2005/0159640 A1* | 7/2005 | Barbut et al. | 600/16 |
| 2005/0245866 A1* | 11/2005 | Azizi | 604/96.01 |
| 2006/0084839 A1* | 4/2006 | Mourlas et al. | 600/116 |
| 2006/0100480 A1* | 5/2006 | Ewers et al. | 600/114 |
| 2006/0253113 A1* | 11/2006 | Arnold et al. | 606/16 |
| 2006/0265000 A1* | 11/2006 | Azizi | 606/200 |
| 2006/0271095 A1* | 11/2006 | Rauker et al. | 606/197 |
| 2006/0287666 A1* | 12/2006 | Saadat et al. | 606/198 |
| 2007/0005041 A1* | 1/2007 | Frassica et al. | 604/544 |
| 2007/0078451 A1* | 4/2007 | Arnold et al. | 606/17 |
| 2007/0142858 A1* | 6/2007 | Bates | 606/200 |
| 2007/0173798 A1* | 7/2007 | Adams et al. | 606/27 |
| 2008/0004606 A1* | 1/2008 | Swain et al. | 606/1 |
| 2008/0215031 A1* | 9/2008 | Belfort et al. | 604/500 |
| 2009/0221997 A1* | 9/2009 | Arnold et al. | 606/15 |
| 2010/0105983 A1* | 4/2010 | Oneda et al. | 600/115 |
| 2010/0228277 A1* | 9/2010 | Pedersen et al. | 606/194 |
| 2011/0160536 A1* | 6/2011 | Blum | 600/116 |

\* cited by examiner

DOUBLE BALLOON ISOLATION CATHETERS AND METHODS THEREFOR

BACKGROUND OF THE INVENTION

1. Field of the Invention

The present invention generally relates to medical devices used for conducting examinations of the colon, and more specifically relates to balloon catheters used for conducting examinations of the colon.

2. Description of the Related Art

FIG. 1 shows the digestive system 20 of a human body, which includes an esophagus 22, a stomach 24 and a liver 26. The stomach 24 is connected to the small intestine 28, which, in turn, is connected to the large intestine or colon 30. The colon 30 has multiple segments including the ascending colon 32, the transverse colon 34 and the descending colon 36. The terminal end of the colon 30 includes the sigmoid colon 38, the rectum 40 and the anus 42. The primary function of the colon is to store unabsorbed waste and to absorb water and other bodily fluids before waste is eliminated through the rectum. A typical colon is about five feet long.

Colon cancer is one of the leading causes of death in the United States. Although the exact cause of colon cancer is undetermined, the disease is influenced by a number of factors including age, lifestyle, and genetics. Although colon cancer may develop at any age, in 90% of cases the individual is 50 years or older. Lifestyle factors such as diet have also been found to influence the incidence of colon cancer. Individuals having diets high in fat and low in fruits and vegetables have an increased risk of developing colon cancer. Other lifestyle factors that increase risk include smoking, alcohol use, sedentary lifestyle, and obesity. Genetics also plays a role in the incidence of colon cancer. Those with a relative in their immediate family having a history of colon cancer are at a higher risk than the general population. Although age, genetic, and lifestyle factors may increase the risk of developing colon cancer, 75% of all colon cancer cases occur in people having no known medical risk factors. Thus, there is a great need for regular colon cancer screening to detect if a patient has a higher risk of developing colon cancer.

A first form of colon cancer screening is commonly referred to as a colonoscopy. During a colonoscopy, a doctor visually examines the inside of the colon to look for inflamed tissue, abnormal growths such as polyps, and ulcers. During a colonoscopy, a doctor will insert a long, flexible, lighted tube into a patient's rectum and slowly guide it into the colon. The tube, commonly referred to as a colonoscope, transmits an image of the inside of the colon onto a display screen so that the doctor may examine the lining of the colon. The colonoscope is flexible so that the doctor may advance it around the curves of the colon. During the procedure, the doctor may remove abnormal growths lining the bowel such as polyps. After removal, the polyps are sent to a lab for further testing.

A second form of colon cancer screening, commonly referred to as a sigmoidoscopy, examines the lower 20 inches of the colon using a lighted, flexible tube. Similar to the colonoscopy procedure, a tube is inserted through the rectum and into the lower portion of the colon to examine the lining of the colon for any abnormalities.

Another colon cancer screening procedure is commonly referred to as a virtual colonoscopy. Virtual colonoscopy can be performed with computed tomography (CT), sometimes referred to as a CAT scan, or with magnetic resonance imaging (MRI). During the virtual colonoscopy procedure, a patient is placed upon an examination table, and a thin tube is inserted into the rectum so that air can be pumped through the tube in order to inflate the colon for better viewing. The examination table is then moved through a scanner to produce cross sections along the length of the colon. A computer program takes the scanned images and creates a three-dimensional picture that can be viewed on a video screen. A virtual colonoscopy is more comfortable than conventional colonoscopy procedures because it does not use a colonoscope. As a result, no sedation is required and the patient may return to his or her usual activities almost immediately. In addition, virtual colonoscopy takes less time than conventional colonoscopies, and provides clearer, more detailed images than barium enema procedures.

A fourth colon cancer screening procedure uses a barium enema. During this procedure, a patient lies on an examination table and a preliminary x-ray is taken. Referring to FIGS. 2A and 2B, a catheter 44 is inserted into the anus 42 so that barium 46 may be introduced into the colon 30. In some devices, a small balloon at the tip of the enema tube is inflated to keep the barium inside the colon. The flow of the barium is monitored by a doctor on an x-ray fluoroscope screen. A gas, such as room air or $CO_2$ Air may be introduced into the colon through the enema tube to distend the colon so as to provide better images on the x-ray fluoroscope screen. During the procedure, the patient is moved into different positions and the examination table is slightly tipped to get different views. At the end of the procedure, the enema tube is removed and the barium is expelled from the colon.

In spite of the above advances, there remains a need for improved tools and methods for conducting colon imaging procedures such as cancer screening.

SUMMARY OF THE INVENTION

The present invention provides devices and methods for selectively isolating a segment of the large intestine using a minimally invasive atraumatic catheter-based design. In one embodiment, the present invention discloses a double balloon isolation catheter whereby the inter-balloon spacing is infinitely adjustable, allowing the physician to selectively isolate a specific segment of the colon while leaving the remainder of the colon undisturbed. Moreover, the present invention reduces the volume of contrast agent that is delivered to the patient, minimizes patient discomfort by distending only the region of the intestine under investigation, overcomes any dysfunction of the ileocecal valve, and reduces overshadowing due to proximally migrating contrast material by isolating a region of colon desired with a proximal and distal balloon providing a predetermined colonic segment for contrast agent infusion. In one embodiment, gas and contrast may be introduced into the colon through a central lumen. The exact level of gas and contrast agent introduced into the colon may be controlled. In one embodiment, a solid-state pressure transducer monitors the pressure within the lumen of the intestine.

The present invention enables medical personnel to isolate a specific region of the large intestine for localized infusion of a contrast agent, such as barium sulfate, for enhanced imaging. In one embodiment, the device isolates a region of the large intestine for pressure distention with the infusion of gas. The device includes a guide wire that provides rapid atraumatic positioning of the catheter along the entire length of the colon for overcoming constricted regions and torturous pathways. In one embodiment, the catheter includes a Thouyborst connector enabling quick deployment and adjustment of the distally located isolating balloon for establishment of an aquastatic and pneumostatic region.

In one embodiment of the present invention, a system for examining the colon includes a catheter having a proximal end, a distal end, and a central lumen extending from the proximal end to the distal end of the catheter, and a flexible tube coupled with the catheter. The system desirably includes a first balloon located adjacent a distal end of the flexible tube, and a second balloon extending around the catheter and being located between the distal and proximal ends of the catheter, whereby the distance between the first and second balloons is adjustable by sliding the flexible tube through the central lumen of the catheter. The first and second balloons are desirably inflatable for isolating a section of a colon for examination.

In one embodiment, the distal end of the catheter has at least one opening for introducing gas into the isolated section of the colon. The distal end of the catheter may have at least one opening for introducing contrast agent into the isolated section of the colon.

In one embodiment, the system includes a guide wire extending through the central lumen of the catheter and the flexible tube. The guide wire desirably has a proximal end accessible at the proximal end of the flexible tube and a distal end extending distally from the distal end of the flexible tube. The proximal end of the guide wire may be manipulated for advancing the distal end of the guide wire through the colon. The distal end of the guide wire may be curved for minimizing the likelihood of perforating the colon wall.

In one embodiment, the system includes a pressure sensor provided on the flexible tube between the first and second balloons. The pressure sensor preferably provides signals to a pressure monitor for monitoring the internal pressure within the isolated colon section. The system may also include a camera provided on the flexible tube for obtaining pictures or video of the colon section being examined.

The system may include at least one connector coupled with the catheter or the flexible tube, such as a Thouy-borst connector, for introducing the gas and/or contrast agent into the isolated section of the colon. The system may also include a pump for introducing the gas and/or contrast agent into the isolated colon section.

In one embodiment of the present invention, a system for examining a colon includes a guide wire insertable into a colon, a flexible tube slidable over the guide wire for advancing the flexible tube into the colon, a first balloon located adjacent a distal end of the flexible tube, and a second balloon located between the first balloon and a proximal end of the flexible tube. The first balloon is preferably movable relative to the second balloon for adjusting the distance between the first and second balloons. The system preferably includes an inlet port located between the first and second balloons for introducing a gas, such as CO.sub.2, into a section of the colon located between the first and second balloons. The system may also include a second inlet port located between the first and second balloons for introducing a contrast agent, such as barium, into the section of the colon located between the first and second balloons.

In one embodiment, the system includes a catheter having a proximal end, a distal end, and a central lumen extending between the proximal and distal ends, whereby the flexible tube is adapted to slide through the central lumen for advancing the flexible tube into the colon. In one embodiment, the first and second inlet ports are located at the distal end of said catheter. The second balloon may extend around the catheter between the first and second inlet ports of the catheter and the proximal end of the catheter. In one embodiment, the flexible tube includes at least one port located between the first and second balloons for introducing gas and/or contrast agent into the colon.

In one embodiment, a method of examining a colon includes defining a section of a colon for examination, forming a first air-tight seal at a first end of the colon section and a second air-tight seal at a second end of the colon section to define an isolated colon section, and introducing a gas, such as air or $CO_2$, into the isolated colon section. The method may also include introducing a contrast agent, such as barium, into the isolated colon section.

In one embodiment, the air-tight seals are formed by positioning a first balloon at the first end of the colon section and a second balloon at the second end of the colon section, and inflating the first and second balloons to form the isolated colon section. The positioning step preferably includes changing the distance between the first and second balloons so that the balloon bound the ends of the colon section under examination.

In one embodiment, the method includes inserting a guide wire into the colon, advancing the guide wire to the first end of the colon section, and coupling the first balloon with the guide wire and advancing the first balloon along the guide wire toward the first end of the colon section. The method may also include providing a rectal catheter having a proximal end, a distal end, and a central lumen extending from the proximal end to the distal end, whereby the second balloon extends around the rectal catheter adjacent the distal end of the rectal catheter, and passing the guide wire through the central lumen of the rectal catheter.

In one embodiment, the present invention reduces the amount of contrast material used by decreasing seepage of the contrast agent past the region of interest.

In one embodiment, the double balloon isolation provides rapid, direct measurement of lumen pressure through an integrated intra-luminal solid-state pressure transducer, thereby enabling a fast, stable, and highly accurate means of continuously monitoring pressure levels within the colon.

In one embodiment, the device includes a side-hole, positioned along the intraluminal segment of the catheter shaft for providing a backup pressure monitoring port with fluid coupling to an external pressure sensor and patient monitor.

In one embodiment, the present invention eliminates overshadowing of x-ray images due to overlapping of contrast from proximal regions of the colon by containing the contrast agent within an area of interest.

In one embodiment of the present invention, a colon cancer screening procedure includes the steps of attaching a pressure transducer to a monitor and zeroing the pressure transducer outside of the body. The method preferably includes loading a guide wire through the central lumen of a rectal catheter and inserting the distal end of the guide wire into the rectum. The guide wire is advanced under fluoroscopic guidance until the guide wire is advanced to or beyond the site of the colon being investigated. The distal end of the catheter is preferably inserted into the rectum and advanced along the guide wire to the desired site. At this point, the distal balloon may be located beyond the desired site of examination. The distal balloon is then desirably inflated so that it engages the inner wall of the intestine. The proximal balloon is then inserted into the rectum and inflated until it engages the rectal wall. The two inflated balloons now define an isolated segment of the colon therebetween. Gas and/or contrast agent may be introduced into the isolated region of the colon located between the two inflated balloons for conducting the colon examination. As the gas and/or contrast agent is introduced into the isolated region of the colon, intra-luminal pressure monitoring may be performed continuously using a pressure transducer. The present invention is not limited to the exact order of the steps outlined herein. Thus, the steps discussed herein may be performed in any order and still fall within the scope of the present invention.

In one embodiment of the present invention, the system includes an integrated video camera for direct visualization of the colon. The video camera may be attached to a flexible tube or catheter.

The present invention provides a number of benefits over prior art devices and methods. First, the double balloon isolation catheter of the present invention has a smaller profile for minimizing patient discomfort. The present invention also provides a device having rapid atraumatic manipulation, location and deployment of the catheter with an over-the-wire design. The present invention also provides infinitely adjustable inter-balloon spacing through movement of the catheter shaft for enabling exact placement of the distal balloon and isolation of the desired colon segment. The present invention also provides for localized delivery of contrast agent and gas for reducing stress on the isolated section of the colon. The present invention also enables pressure distention of the colon for contrast imaging studies in patients having a weakened or incompetent ileocecal valve. The present invention also provides an integrated solid-state pressure transducer that provides rapid and accurate intra-luminal pressure measurements. The present invention also provides a distal inflatable balloon that blocks the migration of contrast agent beyond the site of interest.

In one embodiment, the device or system may include a soft, small diameter, flexible catheter that is designed to minimize patient discomfort. The present invention may also include a video camera integrated therewith to provide direct visualization of the interior of the colon.

These and other preferred embodiments of the present invention will be described in more detail below.

BRIEF DESCRIPTION OF THE DRAWING

So the manner in which the above recited features of the present invention can be understood in detail, a more particular description of embodiments of the present invention, briefly summarized above, may be had by reference to embodiments, which are illustrated in the appended drawing. It is to be noted, however, the appended drawing illustrates only typical embodiments of embodiments encompassed within the scope of the present invention, and, therefore, is not to be considered limiting, for the present invention may admit to other equally effective embodiments, wherein.

DETAILED DESCRIPTION

Figure 1:
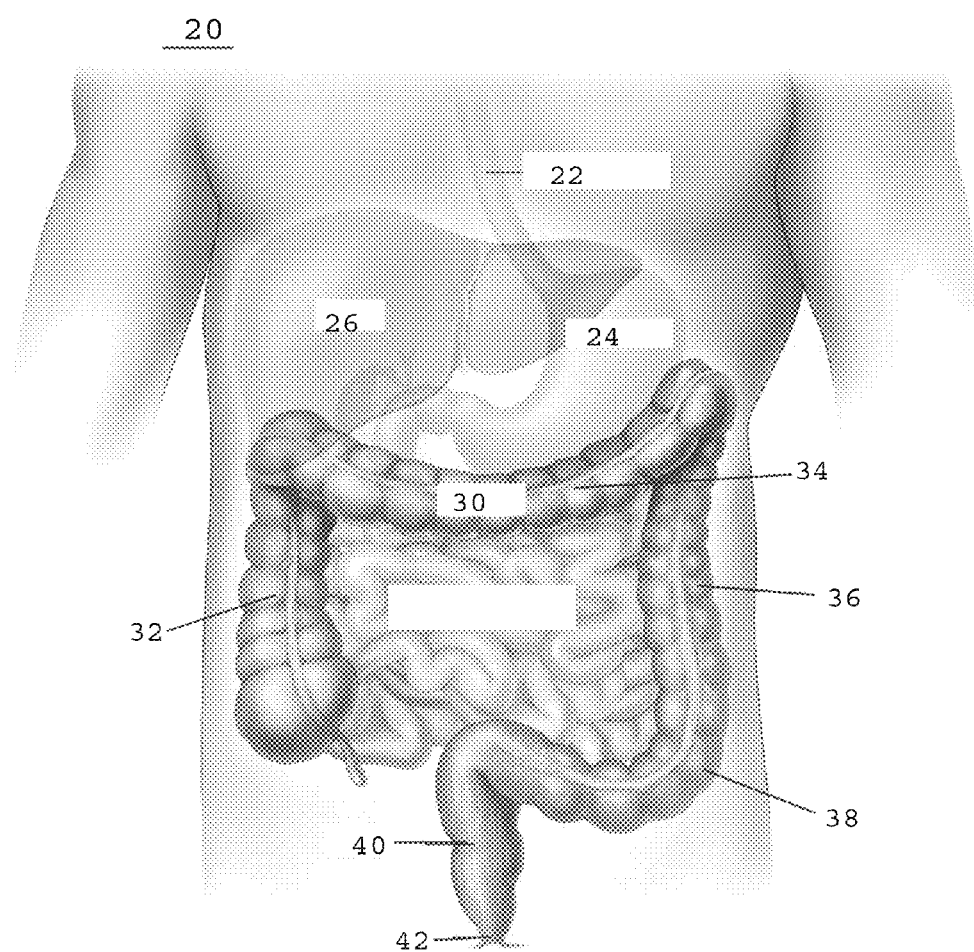
FIG. 1 shows the gastrointestinal (GI) system of a human.
Figure 2A:
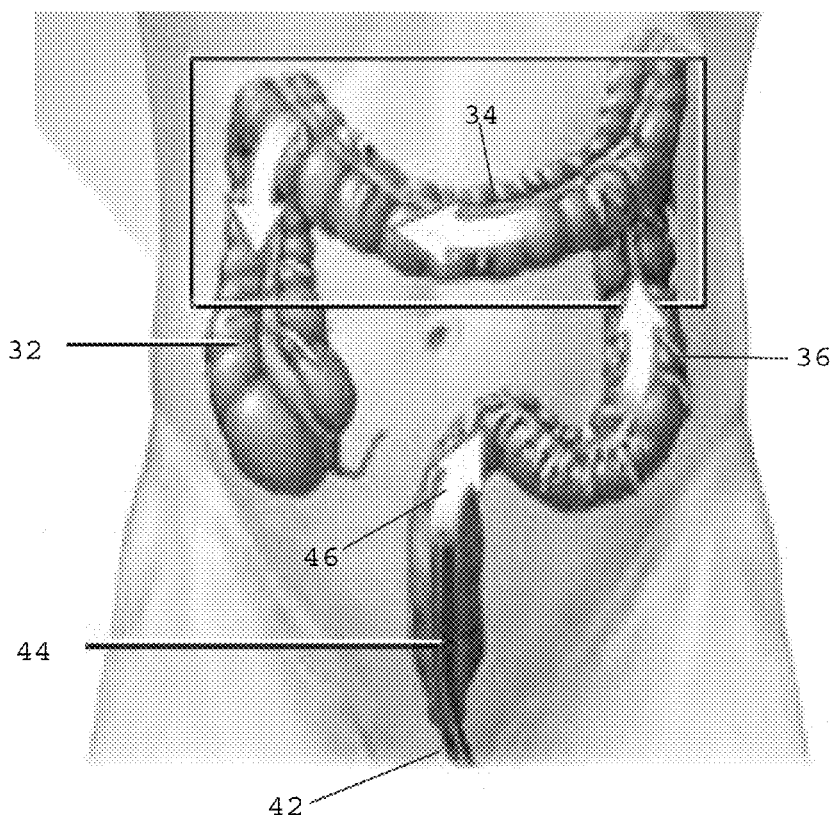
FIGS. 2A and 2B show a conventional colon imaging system that includes a barium enema.
Figure 2B:
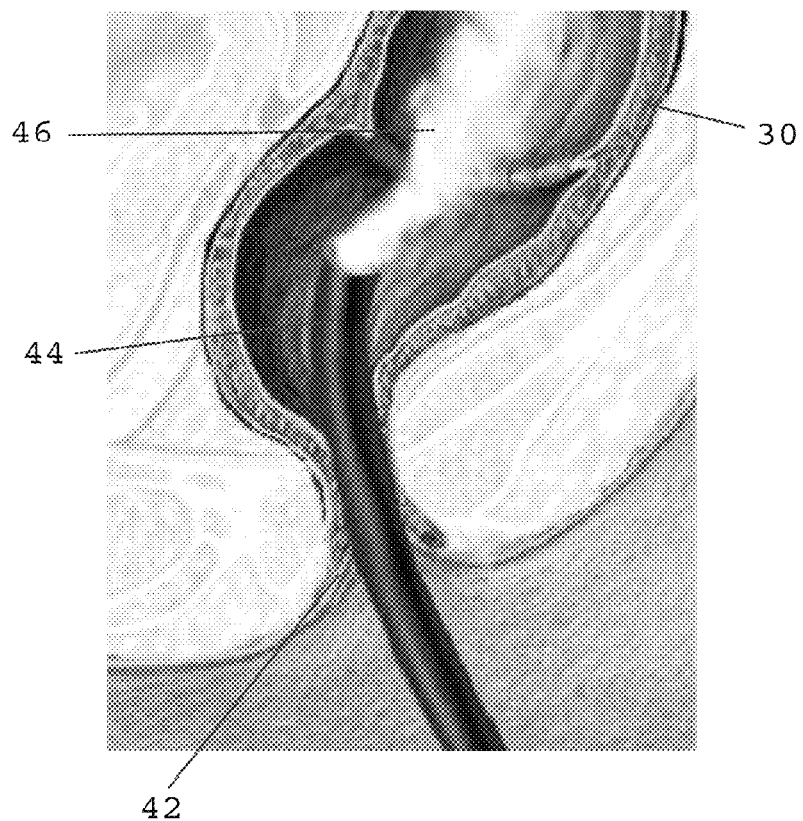

The headings used herein are for organizational purposes only and are not meant to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

Figure 3:
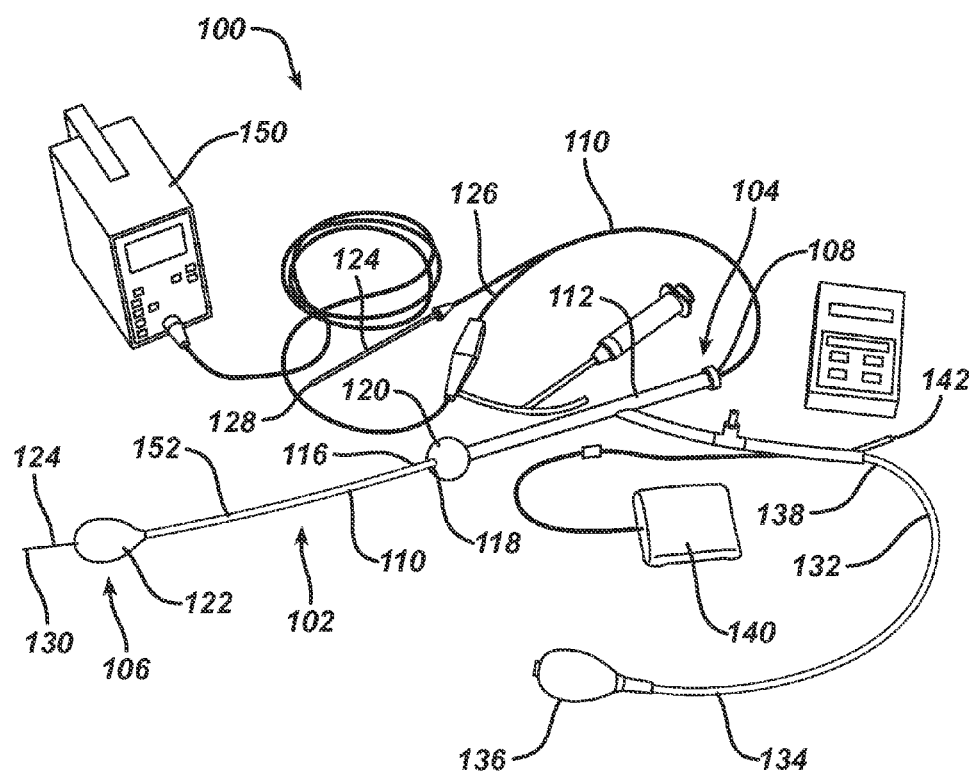
FIG. 3 shows a colon cancer screening system including a double balloon isolation catheter, in accordance with one embodiment of the present invention.

Referring FIG. 3, in accordance with one embodiment of the present invention, a colon cancer screening system 100 includes a double balloon isolation catheter 102 having a proximal end 104 and a distal end 106. The proximal end 104 of the catheter 102 includes a connector 108, such as a Thouyborst connector, having one or more openings. The openings in the connector 108 may be adapted to receive a flexible tube 110, a gas tube, and/or a contrast tube. The connector 108 has a distal end 112 connected to a rectal catheter 114 having a distal end 116 adapted to be inserted into a rectum of a patient. The distal end of 116 of the catheter 114 has one or more openings 118 formed therein through which gas (e.g. $CO_2$) and contrast agent (e.g. barium sulfate) may be infused into a patient's colon.

The double balloon catheter 102 includes an inflatable proximal balloon 120 and an inflatable distal balloon 122. As will be described in more detail below, the distance between the proximal and distal balloons 120, 122 may be adjusted by advancing the flexible tube from an opening provided at the distal 116 of the rectal catheter 114. In one embodiment, the proximal and distal balloons 120, 122 may be inflated and deflated independently relative to one another. In another embodiment, the proximal and distal balloons are inflated and deflated simultaneously.

The system 100 includes a guide wire 124 that passes through a lumen extending through the flexible tube 110. The guide wire 124 desirably has a proximal end 128 that extends proximally of the proximal end 126 of the flexible tube 110, and a distal end 130 that extends distally of the distal balloon 122. As will be described in more detail below, the proximal end of the guide wire 124 may be manipulated by an operator to snake and/or advance the distal end of the guide wire through a patient's colon. After the guide wire has been advanced to a desired location in the colon, the flexible tube 110 may be advanced over the guide wire 124.

The colon cancer screening system 100 includes a gas infusion lumen 132 having a proximal end 134 connected with a hand pump 136 and a distal end 138 coupled with the connector 108. Gas may be introduced into the gas infusion lumen 132 by compressing hand pump 136. The system preferably includes an inflation device 140 for the proximal balloon 120. The system may also include a supply of contrast agent, such as barium sulfate, that may be introduced into the colon through a contrast infusion lumen 142.

The colon cancer screening system 100 desirably includes a pressure monitor 150 that is in communication with a pressure transducer 152 provided on the flexible tube 110. The pressure transducer 152 generates signals that are transmitted to the pressure monitor 150 to provide an indication of the pressure within a colon segment isolated between the proximal and distal balloon 120, 122.

Figure 4:
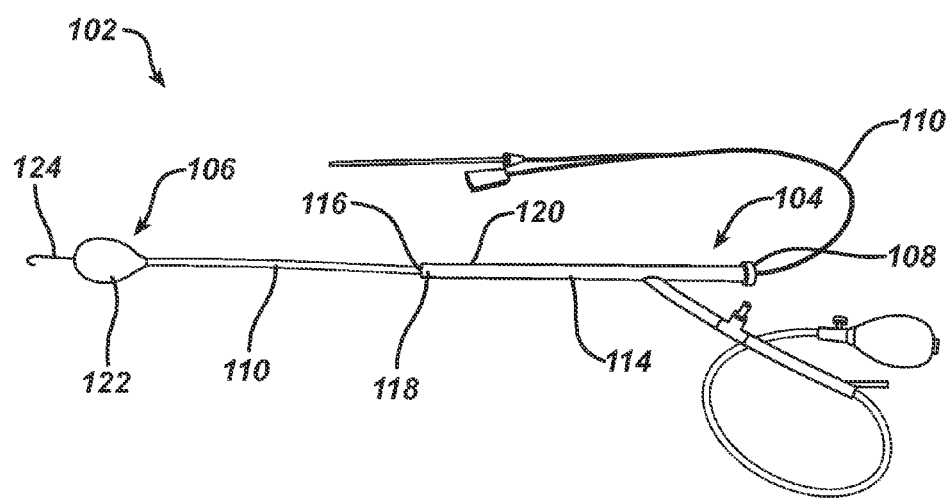
FIG. 4 shows another view of the double balloon isolation catheter of FIG. 3.

FIG. 4 shows another view of the double balloon isolation catheter 102 shown in FIG. 3. The double balloon isolation catheter 102 has a proximal end 104 and a distal end 106, and includes a connector 108 in communication with the rectal catheter 114. The rectal catheter 114 has a distal end 116 with one or more openings 118 for infusing gas and/or contrast media into a patient's colon. The double balloon isolation catheter 102 includes a flexible tube 110 that may be inserted into a proximal opening at a proximal end of the connector 108, and through a distal opening at the distal end 116 of the rectal catheter 114. The flexible tube 110 is preferably of a smaller diameter and flexible so that it may snake and bend when advancing through a patient's colon, thereby minimizing patient discomfort.

In one embodiment, the flexible tube 110 has one or more internal lumens extending therethrough. A first lumen in the flexible tube may be a guide wire lumen through which the guide wire 124 extends. A second lumen in the flexible tube is desirably provided for introducing contrast media into the patient's colon. Another lumen in the flexible tube may be for introducing gas, such as $CO_2$, into the patient's colon for distending or inflating the colon. Still other internal lumens may be provided on the flexible tube 110 for connecting a pressure transducer with a pressure monitor, or a video camera with a video monitor or a display screen.

In the embodiment shown in FIG. 4, the proximal balloon 120 is deflated and the distal balloon 122 is inflated. As will be described in more detail herein, the proximal and distal balloons 120, 122 are preferably inflated to isolate a segment of a patient's colon. When the balloons 120, 122 are inflated, the outer surfaces of the balloons preferably engage the inner wall of the colon to isolate a segment of the colon. In one embodiment, the balloons 120, 122 may be inflated and deflated independently of one another. For example, the proximal balloon 120 may be inflated while the distal balloon 122 is deflated. Once the deflated distal balloon 122 has been advanced to a desired location within the colon, the distal balloon 122 may then be inflated so that both the proximal and distal balloons 120,122 are simultaneously inflated for isolating a segment of the colon.

In one embodiment of the present invention, at least one of the proximal and distal balloons 120, 122 has a spherical shape. In another embodiment, at least one of the proximal and distal balloons may have an oval, oblong, or elongated shape. In one preferred embodiment, the balloons 120, 122 have an elongated shape for increasing the amount of surface contact between the balloon and the inner wall of the colon so as to achieve a reliable air-tight seal without requiring excessive pressure inside the balloon.

In a highly preferred embodiment of the present invention, the flexible tube 110 slides through an opening at the distal end 116 of the rectal catheter 114. As a result, the distance between the distal balloon 122 and the proximal balloon 120 may be modified and adjusted. This distance adjustment feature enables a predetermined segment of the colon to be isolated between the balloons. As a result, only the isolated segment of the colon needs to be distended using gas, and the entire length of the colon does not have to be distended with gas.

Figure 5A:
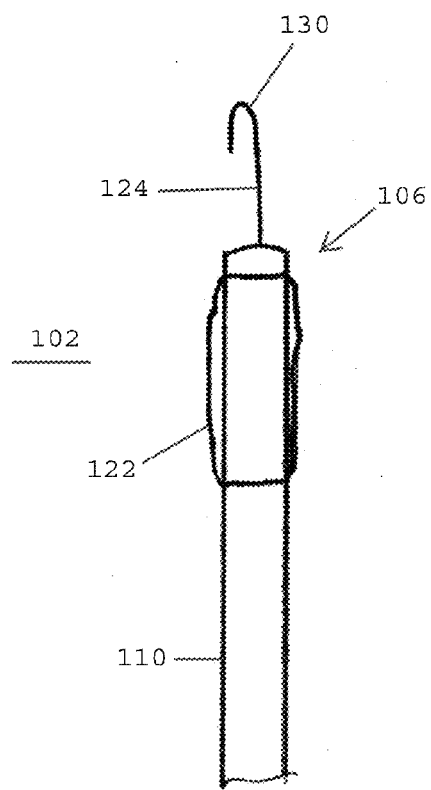
FIG. 5A shows the distal end of the double balloon isolation catheter of FIG. 4 having a distal balloon in a deflated state.
Figure 5B:
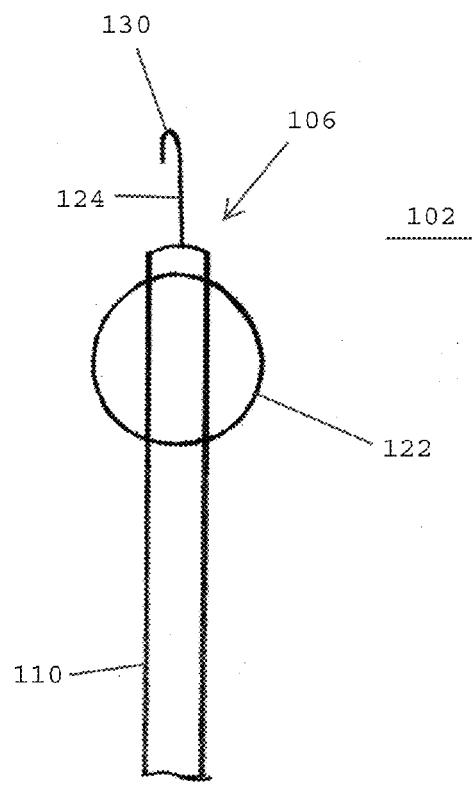
FIG. 5B shows the distal balloon of FIG. 5A in an inflated state.

Referring to FIGS. 5A and 5B, in one embodiment, the distal end 106 of the double balloon isolation catheter 102 has a distal balloon 122 attached thereto, and the distal end 130 of guide wire 124 extends beyond the distal balloon 122. The distal end 130 of guide wire 124 is preferably curved so as to prevent perforations of the colon wall by the guide wire. The guide wire 124 desirably extends through a guide wire lumen provided in the flexible lumen 110. FIG. 5A shows the distal balloon 122 in a deflated state. The distal balloon 122 is desirably maintained in a deflated state as the flexible lumen 110 is advanced over the guide wire. FIG. 5B shows the distal balloon 122 after inflation. The outer walls of the inflated distal balloon 122 desirably engage the inner walls of the colon for forming an air-tight seal with the colon wall. In FIG. 5B, the inflated distal balloon 122 has a spherical shape, however, the balloon 122 may have other shapes such as oval, oblong, etc.

Figures 6A, 6B:
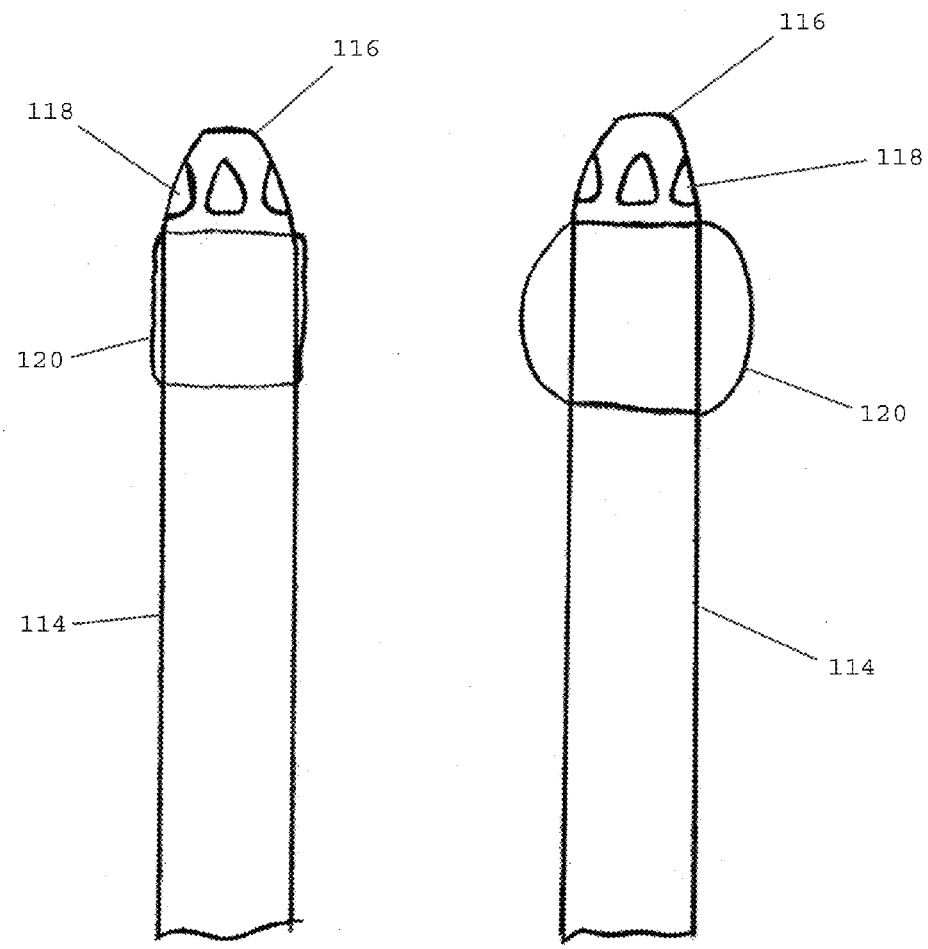
FIG. 6A shows the rectal catheter portion of the double balloon isolation catheter shown in FIG. 4 with the proximal balloon in a deflated state.
FIG. 6B shows the rectal catheter of FIG. 6A with the proximal balloon in an inflated state.

FIGS. 6A and 6B show the rectal catheter 114 portion of the double balloon isolation catheter shown and described above. The rectal catheter 114 has a distal end 116 and a plurality of openings 118 through which gas and/or contrast media may be introduced into a patient's colon. The rectal catheter 114 has a proximal balloon 120 secured adjacent the distal end 116 thereof. After the distal end 116 of the rectal catheter 114 has been inserted into a patient's rectum, the proximal balloon 120 may be inflated to form an air-tight seal with the inner walls of the patient's rectum. FIG. 6A shows the proximal balloon 120 in a deflated state. FIG. 6B shows the proximal balloon 120 after inflation.

Figure 7A:
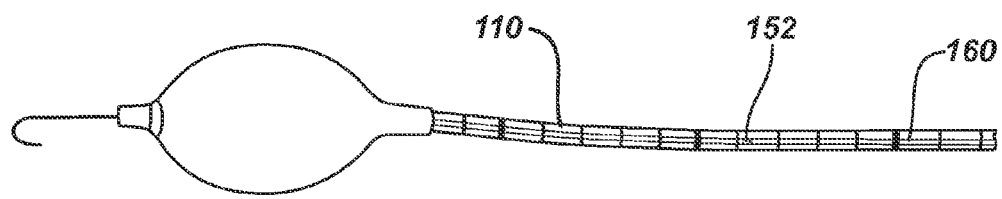
FIG. 7A shows a double balloon isolation catheter having a pressure transducer, in accordance with one embodiment of the present invention.
Figure 7B:
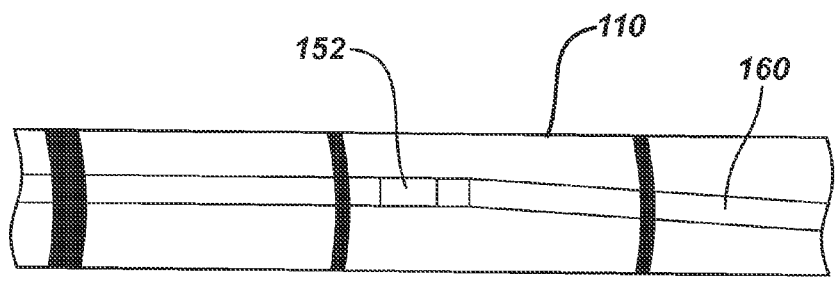
FIG. 7B shows an enlarged view of the pressure transducer shown in FIG. 7A.

Referring to FIGS. 7A and 7B, in one embodiment of the present invention, a pressure transducer 152 is secured to an outer surface of the flexible tube 110. The pressure transducer 152 is in communication with an external pressure monitor 150 (FIG. 3) through a communication line 160. In one embodiment, the communication line 160 extends over an outer surface of the flexible tube 110. In another embodiment, the communication line 160 passes through an internal lumen extending through the flexible tube 110, with the pressure transducer 152 being exposed to an outer surface of the flexible tube 110. The pressure transducer 152 enables the operator to monitor the pressure between the proximal and distal balloons, and within the isolated segment of the colon.

Figure 8:
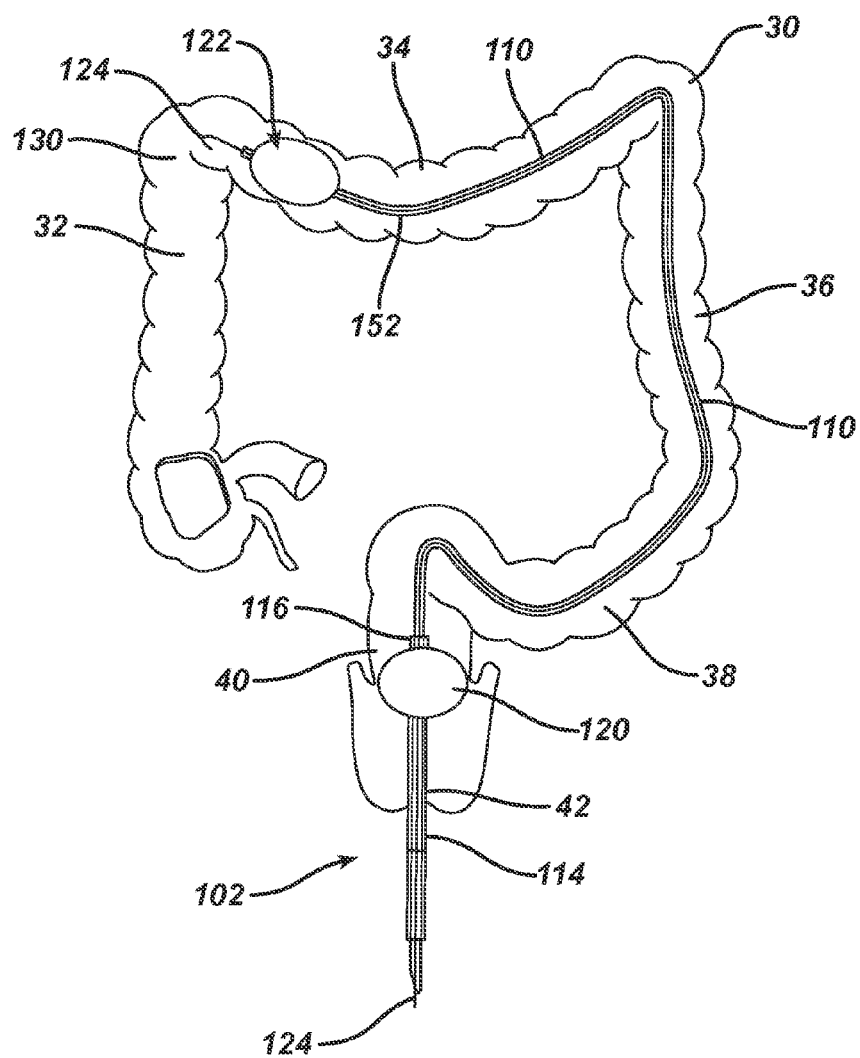
FIG. 8 shows the double balloon isolation catheter of FIG. 4 after being deployed in a colon of a patient, in accordance with one preferred embodiment of the present invention.

FIG. 8 shows a method for deploying a double balloon isolation catheter 102 within the colon of a patient, in accordance with one embodiment of the present invention. In a first preferred step, the guide wire 124 is advanced through the sigmoid colon 38, the descending colon 36 and into the transverse colon 34. After the distal end 130 of the guide wire 124 has been positioned at the desired location within the transverse colon 134, the distal balloon 122 and the flexible tube are advanced over the guide wire 124 until the distal balloon 122 reaches the distal end 130 of the guide wire 124. The rectal catheter 114 is desirably inserted into the patient's anus 42 so that the distal end 116 of the rectal catheter is located in the patient's rectum 40. As a result, the proximal balloon 120 is located in the patient's rectum 40. The proximal and distal balloons 120, 122 may be inflated to isolate a section of the colon 30 therebetween. As used herein, the "isolated" section of the colon is the part of the colon that is located between the proximal and distal balloons 120, 122. A gas, such as $CO_2$, may be introduced into the isolated colon section through the openings at the distal end 116 of the rectal catheter 114. The gas desirably distends the isolated section of the colon so as to enhance the visibility of the isolated colon segment. As the gas is introduced into the colon, the pressure transducer 152 provided on the flexible tube 110 desirably monitors the pressure within the isolated section of the colon. If the pressure rises above a desirable level, some of the gas may be removed through the rectal catheter 114 to lower the pressure within the isolated section of the colon. A contrast medium, such as barium sulfate, may also be introduced into the isolated colon segment through the openings at the distal end 116 of the rectal catheter 114. The contrast medium desirably flows between the proximal balloon 120 and the distal balloon 122. The proximal balloon 122 desirably prevents the gas and/or contrast media from flowing beyond the proximal balloon and into the ascending colon 32. The distal balloon 122 desirably prevents the gas and/or contrast media from escaping from the anus 42

Although the present invention is not limited by any particular theory of operation, it is believed that providing a double balloon isolation catheter, whereby the distance between the proximal and distal balloons may be adjusted, enables an operator to isolate a specific segment of a patient's colon having a specific length. As a result, the entire length of the patient's colon does not need to be distended using a gas. In addition, barium does not have to be introduced into the colon to coat the entire length of the colon. An operator, using the present invention, is able to isolate a shorter, specific segment of the colon and introduce the contrast medium and the infusion gas only into the shorter segment. This result will minimize patient discomfort because only a shorter segment of the colon must be infused with gas and exposed to contrast media. Moreover, the double balloon isolation catheter of the present invention will shorten a medical procedure during a colon cancer screening step.

Figure 9:
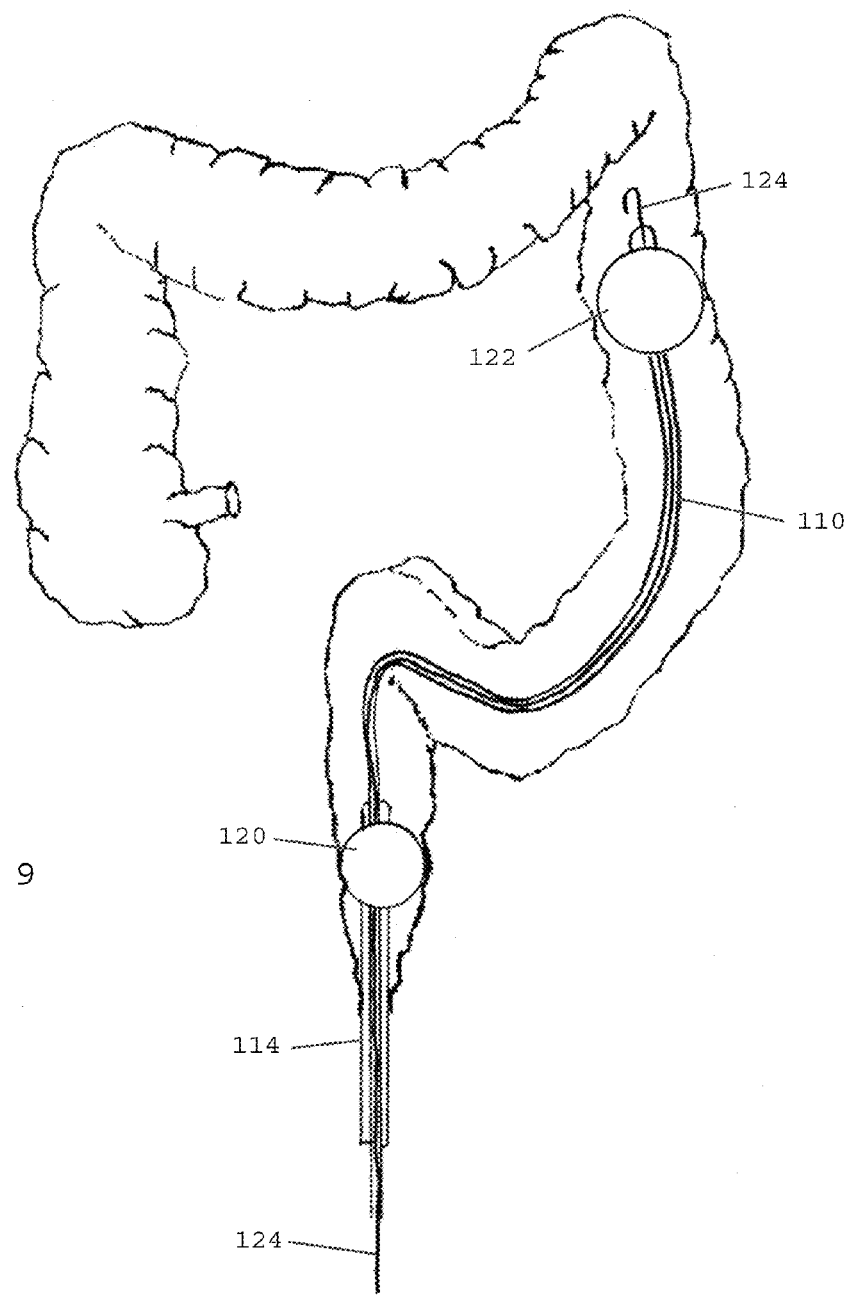
FIG. 9 shows the double balloon isolation catheter of FIG. 8 after the distance between the distal and proximal balloons has been reduced.

Referring to FIG. 9, in one embodiment of the present invention, the distance between the distal balloon 122 and the proximal balloon 120 is reduced. As a result, the length of colon isolated between the proximal and distal balloons 120, 122 is shorter than the length of colon isolated in FIG. 8. After the balloons 120, 122 have been inflated to form air-tight seals at opposing ends of the isolated colon segment gas may be introduced into the isolated colon segment to distend the colon. Contrast medium may also be introduced into the isolated colon segment as part of a barium enema procedure. As noted above, the distance between the distal and proximal balloons 120, 122 may be infinitely modified by advancing the flexible tube 110 over the guide wire 124 or retracting the flexible tube over the guide wire as needed.

Although the present invention is not limited by any particular theory of operation, it is believed that providing a double balloon isolation catheter whereby the distance between the two balloons may be adjusted, enables an operator to minimize the length of the colon that must be inflated with gas and the length of the colon into which contrast medium must be introduced. This provides a number is advantages including reducing patient discomfort, and shortening the time for completing colon cancer screening procedures.

Figure 10:
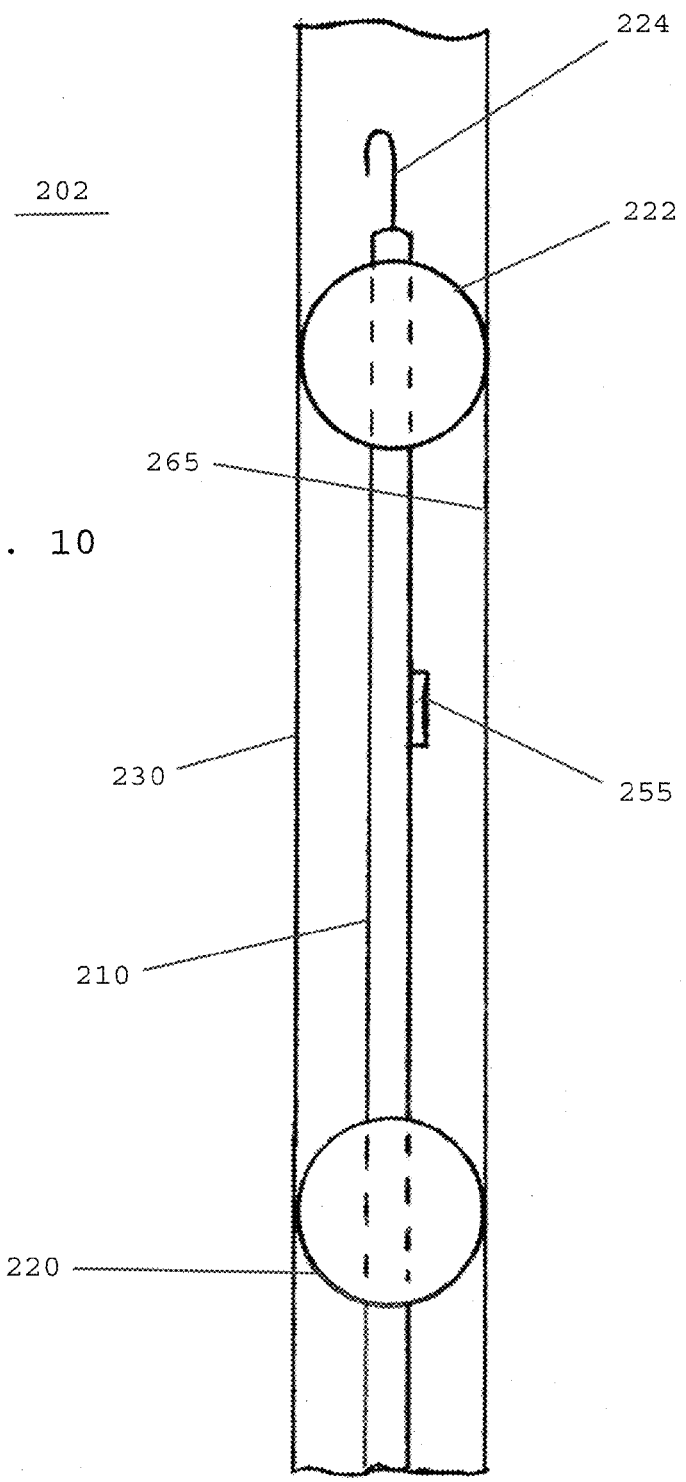
FIG. 10 shows a distal end of a double balloon isolation catheter including a video camera, in accordance with one embodiment of the present invention.

Referring FIG. 10, in one embodiment of the present invention, a double balloon isolation catheter 202 includes a flexible tube 210 and a guide wire 224 projecting beyond the distal end of the flexible tube 210. The double balloon isolation catheter 202 includes an inflatable proximal balloon 220, an inflatable distal balloon 222, and a camera 255 secured to the flexible tube 210. The camera 255 preferably enables an operator to obtain video or photos of the inner wall 265 of the colon 230. The video images captured by the camera 255 are preferably transferred out of the body to a video monitor for observation by a physician or medical personnel.

Figure 11:
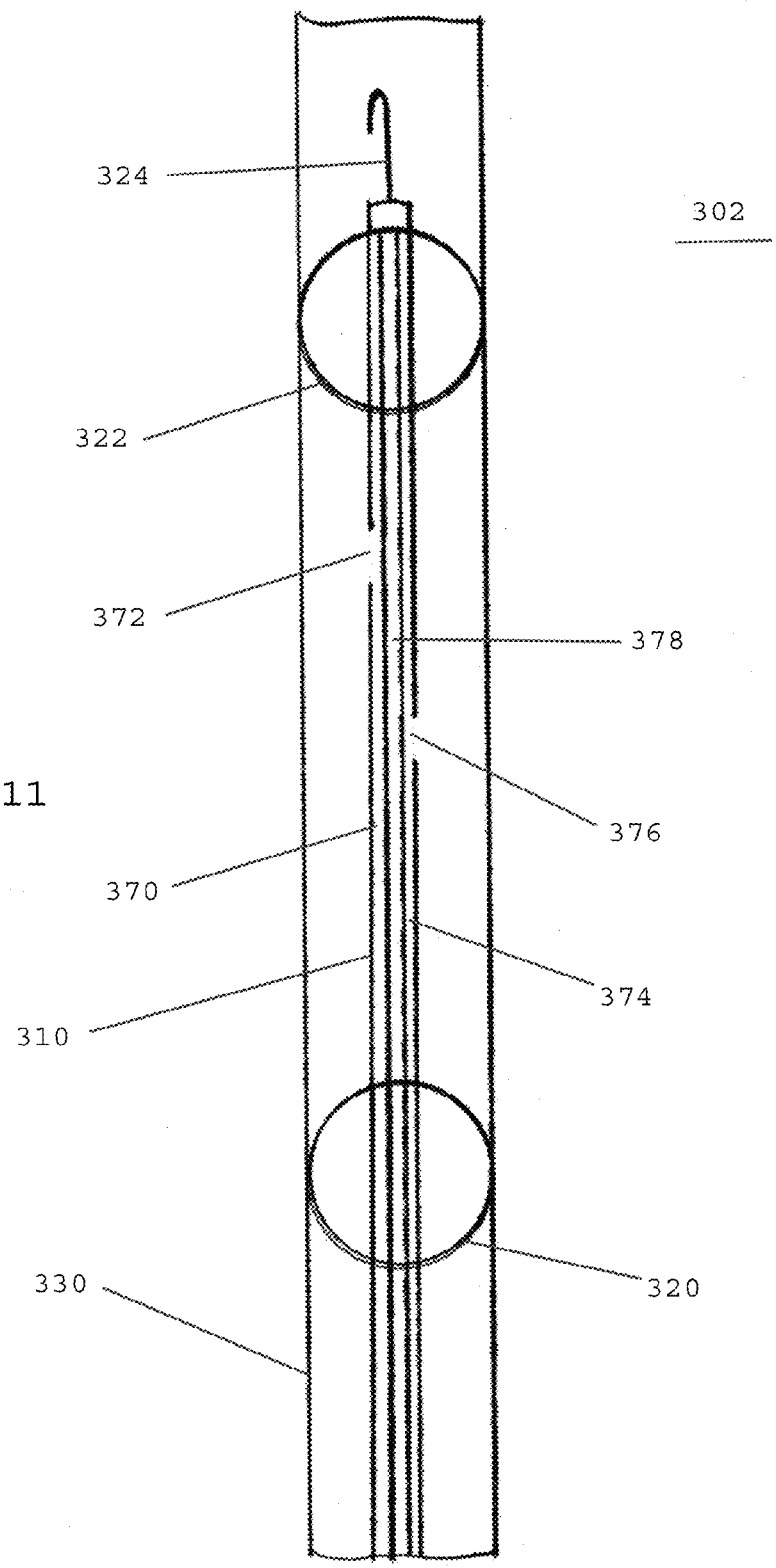
FIG. 11 shows a distal end of a double balloon isolation catheter including ports for introducing gas and/or contrast agent into an isolated section of a colon, in accordance with one embodiment of the present invention.

Referring to FIG. 11, in one preferred embodiment of the present invention, a double balloon isolation catheter 302 includes a flexible tube 310 having a plurality of internal lumens extending therethrough. As shown in FIG. 11, the flexible tube 310 includes a first lumen 370 for introducing gas through a first port 372 and into the isolated colon segment. The flexible tube 310 also has a second internal lumen 374 having a second port 376 for introducing contrast medium into the isolated colon segment. The flexible tube 310 also includes a guide wire lumen 378 through which the guide wire 324 may pass.

In one embodiment, after the flexible tube 310 has been advanced to a desired location within the colon, the proximal and distal balloons 320, 322 may be inflated to form air-tight seals with internal walls of the colon 330 so as to isolate a segment of the colon. Gas, such as $CO_2$, may be introduced into the isolated colon segment through the first port 372. The pressure within the isolated colon segment may be monitored using a pressure transducer, as described above. A contrast medium, such as barium sulfate, may be introduced into the isolated colon segment through the second port 376. As is well known to those skilled in the art, the contrast medium facilitates conducting the colon cancer screening examination. After the screening procedure is complete, the gas may be withdrawn from the isolated colon segment through the first port 372, and the barium may be discharged through the anus.

Figure 12:
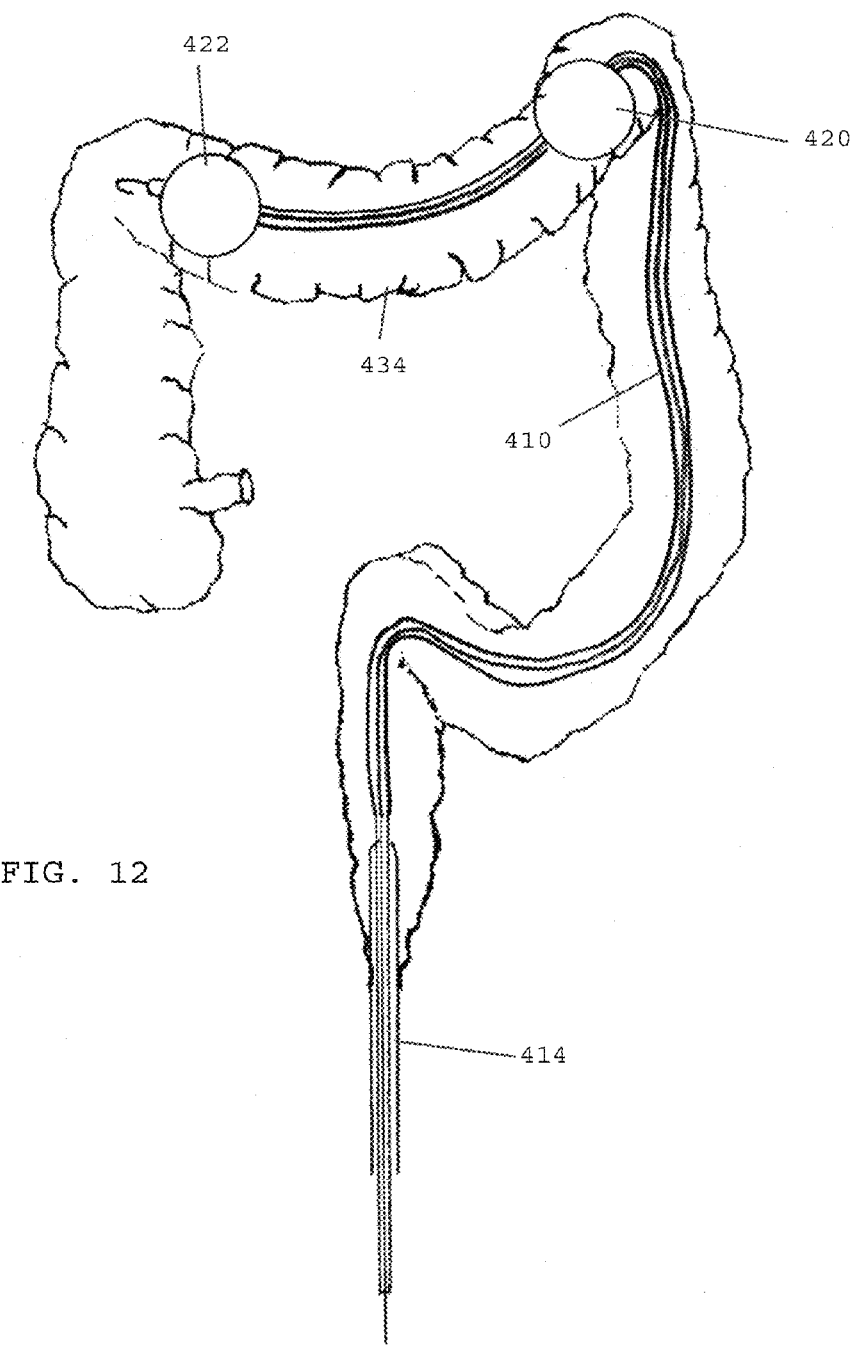
FIG. 12 shows a double balloon isolation catheter, in accordance with another preferred embodiment of the present invention.

Referring to FIG. 12, in one embodiment of the present invention, a double balloon isolation catheter 402 includes proximal and distal balloons 420, 422 that may be positioned anywhere along the length of a flexible tube 410. As such, the proximal balloon 420 is not required to be attached to the rectal catheter 414 as described above. As shown in FIG. 12, the distal balloon 422 may be advanced over the flexible tube 410 to a positioned at the beginning of the transverse colon 434 and the proximal balloon 420 may be advanced over the flexible tube 410 to a position at the end of the transverse colon 434. The balloons 420, 422 may be inflated to isolate a colon segment that extends completely within the transverse colon segment. Gas and contrast media may then be introduced into the isolated transverse colon segment 434 to conduct a colon cancer screening procedure.

Although the FIG. 12 embodiment is not limited by any particular theory of operation, it is believed that providing a double balloon isolation catheter 402 having a proximal balloon 420 that is movable over the flexible tube 410 enables an operator to isolate an even smaller segment of the colon for cancer screening or examination. Thus, the embodiment shown in FIG. 12 further improves efficiencies and further minimizes patient discomfort.

Although many of the embodiments described above utilize contrast medium, such as barium, it is contemplated that the present invention may be utilized without requiring a contrast medium. Thus, in one embodiment of the present invention, the double balloon isolation catheter may be utilized to isolate a colon segment and only gas may be introduced into the isolated colon segment, without using contrast media. For example, the double balloon isolation catheter of the present invention may be utilized during a virtual colonoscopy to isolate a smaller segment of the colon and to introduce only gas (without contrast media) into the isolated colon segment. The present invention may also be used to conduct colonoscopies and sigmoidoscopies, as well as other well-known cancer screening procedures.

While the foregoing is directed to embodiments of the present invention, other and further embodiments of the invention may be devised without departing from the basic scope thereof.

What is claimed is:

1. A system for examining a colon comprising:
a catheter having a proximal end, a distal end, and a central lumen extending from the proximal end to the distal end;
a flexible tube extending through the central lumen of said catheter, said flexible tube having a proximal end that extends proximally beyond the proximal end of said catheter and a distal end that extends distally beyond the distal end of said catheter, said flexible tube being of sufficient length to extend from the anus to the sigmoid colon of an adult human;
a first balloon secured to said flexible tube adjacent the distal end of said flexible tube; and
a second balloon secured to and extending around said catheter, said second balloon being proximal to the distal end of said catheter, wherein the distance between said first and second balloons is adjustable by engaging the proximal end of said flexible tube that extends proximally beyond the proximal end of said catheter for sliding said flexible tube through the central lumen of said catheter, and wherein the distal end of said flexible tube that extends distally beyond the distal end of said catheter is adapted to bend for tracking the path of the colon from the anus to the sigmoid colon as said flexible tube is advanced through the colon, wherein said catheter is a rectal catheter that tapers inwardly between said second balloon and the distal end of said rectal catheter for insertion into a patient's anus so that said second balloon is located in the patient's rectum and the proximal end of said rectal catheter projects outside the patient's anus.

2. The system as claimed in claim 1, wherein said first and second balloons are inflatable for isolating a section of the colon.

3. The system as claimed in claim 2, wherein said rectal catheter has at least one opening for introducing gas into the isolated section of said colon, the at least one opening for introducing gas being distally located relative to said second balloon and proximal to the distal end of said rectal catheter, and wherein said second balloon is inflatable for forming an air-tight seal with inner walls of the patient's rectum.

4. The system as claimed in claim 3, wherein said rectal catheter has at least one opening for introducing contrast agent into the isolated section of said colon, the at least one opening for introducing contrast agent being distally located relative to said second balloon and proximal to the distal end of said rectal catheter.

5. The system as claimed in claim 1, further comprising a guide wire extending through the central lumen of said catheter and said flexible tube, wherein said guide wire has a proximal end accessible at the proximal end of said flexible tube that extends proximally beyond the proximal end of said catheter and a distal end that extends distally beyond the distal end of said flexible tube.

6. The system as claimed in claim 5, wherein the distal end of said guide wire is curved.

7. The system as claimed in claim 1, further comprising a pressure sensor provided on said flexible tube between said first and second balloons.

8. The system as claimed in claim 1, further comprising a camera provided on said flexible tube.

9. The system as claimed in claim 3, further comprising at least one connector coupled with the proximal end of said flexible tube that extends proximally beyond the proximal end of said rectal catheter for introducing said gas into the isolated section of said colon.

10. The system as claimed in claim 9, further comprising a pump for introducing said gas into said isolated colon section.

11. The system as claimed in claim 1, wherein said flexible tube is of sufficient length to extend from the anus to the transverse colon of an adult human and wherein said flexible tube is adapted to bend for tracking the path of the colon from the anus to the transverse colon as said flexible tubing is advanced distally through the colon.

12. The system as claimed in claim 1, wherein the proximal end of said flexible tube that extends proximally beyond the proximal end of said rectal catheter is accessible for adjusting the distance between said first and second balloons, wherein the distance between said first and second balloons increases as the proximal end of said flexible tube is advanced distally toward the proximal end of said rectal catheter and decreases as the proximal end of said flexible tube moves proximally away from the proximal end of said rectal catheter.

13. A system for examining a colon comprising:
a catheter having a proximal end, a distal end, and a central lumen extending from the proximal end to the distal end of said catheter;
a proximal balloon secured to and extending around said catheter;
a flexible tube passing through the central lumen of said catheter, said flexible tube having a proximal end and a distal end;
a distal balloon secured to said flexible tube, said distal balloon being located adjacent the distal end of said flexible tube;
the proximal end of said flexible tube extending proximally beyond the proximal end of said catheter;
the distal end of said flexible tube extending distally beyond the distal end of said catheter;
wherein said catheter is a rectal catheter that tapers inwardly between said second balloon and the distal end of said rectal catheter for insertion into a patient's anus so that said proximal balloon is located in the patient's rectum and the proximal end of said rectal catheter projects outside the patient's anus;
wherein the distance between said distal balloon and said proximal balloon is decreased by moving the proximal end of said flexible tube in a proximal direction away from the proximal end of said rectal catheter, and wherein the distance between said distal balloon and said proximal balloon is increased by moving the proximal end of said flexible tube in a distal direction toward the proximal end of said rectal catheter.

14. The system as claimed in claim 13, wherein said proximal and distal balloons are inflatable for isolating a section of the colon.

15. The system as claimed in claim 14, wherein said rectal catheter has at least one opening at the distal end thereof for introducing gas or contrast agent into the isolated section of said colon, the at least one opening for introducing gas or contrast agent being distal to said proximal balloon and proximal to the distal end of said rectal catheter.

16. The system as claimed in claim 13, further comprising a guide wire extending through the central lumen of said catheter and said flexible tube, wherein said guide wire has a proximal end that extends proximally beyond the proximal end of said flexible tube and a distal end that extends distally beyond the distal end of said flexible tube.

17. The system as claimed in claim 16, wherein the distal end of said guide wire is curved.

18. The system as claimed in claim 13, further comprising a pressure sensor provided on said flexible tube.

19. The system as claimed in claim 13, further comprising a camera provided on said flexible tube.

20. The system as claimed in claim 13, wherein said flexible tube has a non-threaded outer surface.

* * * * *